United States Patent [19]

Nádor et al.

[11] Patent Number: 5,096,902
[45] Date of Patent: Mar. 17, 1992

[54] HETEROCYCLIC COMPOUNDS CONTAINING NITROGEN AND SULFUR, PHARMACEUTICAL COMPOSITIONS CONTAINING THEM AND PROCESS FOR PREPARING SAME

[75] Inventors: Károly Nádor; Pál Scheiber; née Szelecsényi Andräsi; Bela Molnár; László Szporny; Béla Kiss; Egon Kárpáti; Éva Pálosi; Dóra Groó; István Laszlovszky; Zsolt Szombathelyi; Ádám Sarkadi; Anikó Gere; Mihály Bodó; Katalin Csomor; Judit Laszy; Zsolt Szentirmay, all of Budapest, Hungary

[73] Assignee: Richter Gedeon Vegyeszeti Gyar Rt., Budapest, Hungary

[21] Appl. No.: 509,473

[22] Filed: Apr. 12, 1990

[30] Foreign Application Priority Data

Jul. 11, 1989 [HU] Hungary ............................ 3474/89

[51] Int. Cl.[5] .................. C07D 277/04; C07D 279/06; A61K 31/425; A61K 31/54
[52] U.S. Cl. .................. 514/226.8; 514/326; 514/365; 544/54; 546/280; 548/146; 548/201
[58] Field of Search .................. 548/146, 201; 544/54; 546/280; 514/365, 326, 226.8

[56] References Cited

U.S. PATENT DOCUMENTS 4,652,649 3/1987 Daus ..................... 546/146
4,656,286 4/1987 MacGregor .................. 548/146

Primary Examiner—Robert Gerstl
Attorney, Agent, or Firm—Herbert Dubno; Jonathan Myers

[57] ABSTRACT

The invention relates to novel nitrogen- and sulfur-containing heterocyclic compounds of the formula (I), acid addition salts thereof, pharmaceutical compositions containing them and a process for their preparation. In the formula (I)

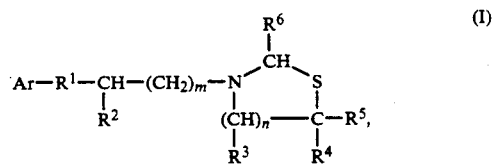

Ar stands for an optionally mono- or polysubstituted aryl or heteroaryl group;
$R^1$ means a carbonyl or ($C_{2-6}$alkenyl)carbonyl group;
$R^2$ stands for hydrogen $C_{1-6}$alkyl, phenyl or phenyl ($C_{1-4}$alkyl) group;
$R^3$ means hydrogen or ($C_{1-6}$alkoxy)carbonyl group;
$R^4$ and $R^5$ stand, independently from each other, for hydrogen or $C_{1-6}$alkyl group;
$R_6$ ogen, $C_{1-6}$alkyl group or halophenyl group;
m is 0 or 1; and
n is 1 or 2, with the proviso that $R^2$ means hydrogen when m is 0.

The compounds of formula (I) show a significant cerebral antihypoxic action and thus, they can be used for the treatment of diseases caused by hypoxic brain damages such as e.g. the senile dementia, Alzheimer's disease or disturbances of the cognitive function.

16 Claims, No Drawings

HETEROCYCLIC COMPOUNDS CONTAINING NITROGEN AND SULFUR, PHARMACEUTICAL COMPOSITIONS CONTAINING THEM AND PROCESS FOR PREPARING SAME

The invention relates to novel, nitrogen- and sulfur-containing heterocyclic compounds of the formula (I)

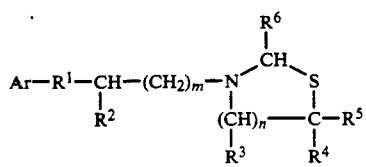

wherein
- Ar stands for an optionally mono- or polysubstituted aryl or heteroaryl group;
- $R^1$ means a carbonyl or a ($C_{2-6}$alkenyl)carbonyl group;
- $R^2$ stands for hydrogen, a $C_{1-6}$alkyl, phenyl or phenyl ($C_{1-4}$alkyl) group;
- $R^3$ means hydrogen or a ($C_{1-6}$alkoxy)carbonyl group;
- $R^4$ and $R^5$ stand, independently from each other, for hydrogen or a $C_{1-6}$alkyl group;
- $R^6$ means hydrogen, a $C_{1-6}$alkyl group or a halophenyl group;
- m is 0 or 1; and
- n is 1 or 2, with the proviso that $R^2$ means hydrogen when m is 0, as well as their acid addition salts and pharmaceutical compositions containing these compounds. Furthermore, the invention relates to a process for the preparation of these compounds.

The compounds of formula (I) according to the invention are biologically active: they possess a significant cerebral antihypoxic action.

In the compounds of the formula (I), the "aryl" substituent means a phenyl group optionally annelated with an other aromatic ring; preferably a phenyl, naphthyl or phenanthrenyl, more preferably a phenyl group.

"Heteroaryl" group means a 5-membered heterocyclic group containing sulfur or oxygen as a heteroatom, a preferred representative of which is the thienyl group.

The aryl and heteroaryl groups may be mono- or polysubstituted by a halogen, $C_{1-6}$alkyl, $C_{1-6}$alkoxy, nitro, phenyl($C_{1-4}$alkoxy), $C_{1-6}$alkylthio, $C_{1-6}$alkylsulfinyl, halophenyl, phenyl or piperidino group.

The alkyl moieties either alone or as a part of other groups include straight or branched chain saturated groups which, depending on the defined number of carbon atoms, may be e.g. methyl, ethyl, n- or isopropyl, n-, sec- or tert-butyl as well as n- or isopentyl and n- or isohexyl groups.

In the meaning of $R^1$, the ($C_{2-6}$alkenyl)carbonyl moiety is preferably an ethylenecarbonyl group.

"Halogen" means fluorine, chlorine, bromine or iodine as substituent.

In the meaning of $R^2$, the phenyl($C_{1-4}$alkyl) preferably stands for a benzyl group.

Depending of the value of m, the compounds of the formula (I) can be considered to be α- or β-aminoketones, the nitrogen atom of which is simultaneously the member of a heterocyclic ring containing a sulfur atom as well.

β-Aminoketones (in other words: Mannich ketones) are well known. Their chemical properties are reviewed inter alia in: F. F. Blicke: Organic Reactions, Vol. 1, page 303 to 341, J. Wiley, New-York, London (1942); B. Reichert: Die Mannich-Reaktion, Springer Verlag, Berlin, Göttingen-Heidelberg, (1959); as well as H. Hellmann and G. Opitz: α-Aminoalkylierung, Verlag Chemie, Weinheim/Bergstr. (1960).

The types of compounds described until now in this field are very different and the number of the specifically described substances is very high. From a therapeutical point of view more significant β-ketones are e.g. propipocaine hydrochloride [3-(1-piperidinyl)-1-(4-propoxyphenyl)-1-propanone], a local anaesthetic agent described in DD patent specifications Nos. 9330 and 9565; tolperisone hydrochloride, [2-methyl-1-(4-methylphenyl)-3-(1-piperidinyl)-1-propanone], a vasodilator and centrally acting muscle relaxant disclosed in the HU patent specification No. 144,997; oxyphedrine hydrochloride [R(R*,S*)-3-(2-hydroxy-1-methyl-2-phenylethyl)-amino-1-(3-methoxyphenyl)-1-propanone] described in the DE patent specification No. 1,439,574; as well as the α-receptor blocking 6-[3-(3-phenylpyrrolidinyl)propionyl]-benzodioxane described in the published DE application No. 2,252,344.

M. Celadnik, K. Palat, A. Sehere and C. Vrba [Arch. Pharm. 291, 3 (1958)] described two β-aminoketones substituted by a thiomorpholinyl group; a local anaesthetic effect is mentioned.

Among the δ-aminoketones structurally related to the compounds of the formula (I), haloperidol [4-[4-(4-chlorophenyl)-4-hydroxy-1-piperidinyl]-1-(4-fluorophenyl)-1-butanone], a neuroleptic drug should be mentioned, of which a high number of structural analogues are known. Pitenodil [2-[4-(3-thenoylpropyl)-1-piperazinyl]ethyldimethylcarbamate] an antihypertensive agent, belongs to this class of compounds, too. Methadone (6-dimethylamino-4,4-diphenyl-3-heptanone) an analgesically acting γ-aminoketone, is described in the DE patent specifications Nos. 865,314 and 870,700.

When n is 1, the compounds of the formula (I) are thiazolidine derivatives. Quite few pharmacologically active thiazolidine derivatives are only known: as an example nitrodan [3-methyl-5-(4-nitrophenylazo)-2-thioxo-4-thiazolidinone], an anthelmintic drug, may be mentioned.

When n is 2, the compounds of the formula (I) are tetrahydro-1,3-thiazine derivatives. From the structurally similar compounds, xylazine containing a 5,6-dihydro-4H-1,3-thiazine skeleton does not belong to the class of the aminoketones. Xylazine is a surgical analgesic used in the veterinary medicine.

Surprisingly, it has been found that the compounds of the formula (I), wherein Ar, $R^1$, $R^2$, $R^3$, $R^4$, $R^5$, $R^6$, n and m are the same as defined for the formula (I), possess a significant cerebral antihypoxic activity.

The antihypoxic activity was investigated on conscious mice under normobaric hypoxia. Five male mice each were placed in a glass cylinder of 3 liters volume, which a gaseous mixture containing 96% of nitrogen and 4% of oxygen was bubbled through. The interval passing from the accomodation of the animals until the cessation of their respiratory movement was registered as survival time. Animals surviving a time of two times as long as that of the control group, were considered to be protected.

Ten animals each were intraperitoneally (i.p.) given a dose of 50 mg/kg of body-weight (hereinafter abbreviated: mg/kg) each of the substances 30 minutes before the accommodation in the glass cylinders. The average time of survival, the percentage of elongation of survival time in comparison to that of the control group and the percentage of the animals protected are shown in Table I.

TABLE I

| Substance of Example No. | Survival min. | time % | Protection % |
|---|---|---|---|
| Control | 6.32 | 100 | 0 |
| 1 | 9.35 | 148 | 30 |
| 8 | 8.27 | 131 | 20 |
| 34 | 12.76 | 202 | 70 |
| 17 | 11.00 | 174 | 60 |
| 18 | 10.58 | 167 | 50 |
| 19 | 7.90 | 125 | 20 |
| 22 | 9.27 | 147 | 30 |
| 49 | 9.72 | 154 | 30 |
| Control | 5.78 | 100 | 0 |
| 12 | 10.28 | 178 | 40 |
| 35a | 10.75 | 186 | 60 |
| 20 | 7.85 | 136 | 20 |
| 30 | 8.40 | 145 | 40 |
| 37 | 12.22 | 211 | 60 |
| 38 | 9.95 | 172 | 30 |
| 39 | 10.43 | 180 | 40 |
| 41 | 8.91 | 154 | 20 |
| Control | 3.05 | 100 | 0 |
| 27 | 5.32 | 174 | 20 |
| 70 | 5.78 | 189 | 60 |

It is obvious from the data of Table I that all compounds prepared according to the various Examples possess an antihypoxic activity appearing in the elongation of survival time.

The antihypoxic effect of the compounds according to the invention was proven also by using the methods of asphyxial anoxia and hypobaric hypoxia. These investigations were carried out by oral administration also proving the oral efficiency which makes possible use of the active compounds according to the invention in a tablet form.

The methods used are described hereinafter.

The Asphyxial Anoxia Test [C. Caillard et. al.: Life Sci. 16, 1607 (1975)]

Mice starved for 16 hours were orally treated with the compounds according to the invention and after one hour, they were placed into well-closed glass bottles of 100 ml volume. The interval passing from closing the bottle until the cessation of the respiratory movement was registered as survival time. Animals surviving longer by 30% than that of average survival time of the control group, were considered to be protected.

The Hypobaric Hypoxia Test [J. Baumel et al.: Proc. Soc. Exptl. Biol. NY. 132, 629 (1969)]

Mice starved for 16 hours were orally treated with the compounds according to the invention, and placed into a desiccator one hour following the treatment. The pressure in the desiccator was reduced to 170 Hgmm within 20 seconds and the survival time was registered from this time until the cessation of respiratory movement. Animals surviving twice as long as the average survival time of the control group were considered to be protected.

In the cases of both methods, the ED$_{50}$ values, i.e. the dose protecting half of the treated animals from the hypoxia, were calculated by using probit analysis.

The results of investigations on the antihypoxic effect after oral treatment are summarized in Table II.

TABLE II

| Substance of Example No. | Oral ED$_{50}$ mg/kg | |
|---|---|---|
| | Asphyxial anoxia | Hypobaric hypoxia |
| 35a | 18.3 | 58.7 |
| 17 | 55.0 | 60.0 |

The data of Table II show the compounds of the invention to possess an oral efficiency, too. The 4-fluorophenyl substitution seems to be particularly preferred.

The antihypoxic effect of the compounds can also therapeutically be used with advantage in hypoxic brain damage of various origin such as senile dementia, Alzheimer's disease, hypoxia following atherosclerosis, multi-infarctual dementia and disturbances of the cognitive function. The therapeutic dose amounts to 0.1 to 40 mg/kg.

The toxicity of the active compound of Example 35a according to the invention was determined on mice. The LD$_{50}$ value of the active compound was found to be 646 mg/kg orally and 108 mg/kg intravenously.

According to an other aspect of the invention, there is provided a process for the preparation of the compounds of formula (I) and their acid addition salts, which comprises a) reacting a ketone of the formula (IV)

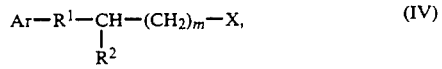

wherein Ar, $R^1$, $R^2$ and m are as defined above and X stands for halogen, with a heterocyclic compound of the formula (III)

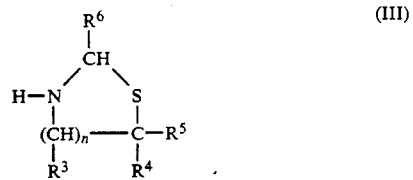

containing sulfur and nitrogen, wherein $R^3$, $R^4$, $R^5$, $R^6$ and n are as defined above, and, if desired, converting the compound of the formula (I) obtained into its acid addition salt: or b) reacting a ketone of the formula (II)

wherein Ar, $R^1$ and $R^2$ are as defined above, with a salt of a heterocyclic compound of the formula (III) containing sulfur and nitrogen, wherein $R^3$, $R^4$, $R^5$, $R^6$ and n are as defined above, and with formaldehyde or a formaldehyde source to obtain compounds of the formula (I), wherein Ar, $R^1$, $R^2$, $R^3$, $R^4$, $R^5$, $R^6$, n are as defined above and m is 1.

According to a preferred embodiment of the process a) of the invention, the base form of a heterocyclic compound of the formula (III) is reacted with a halogen derivative of the formula (IV) in a polar solvent such as acetone, ethanol or acetonitrile, in the presence of an acid binding agent which is capable to bind the HX acid formed in the reaction. Lower tertiary amines, preferably triethylamine or 1-methylpiperidine, or salts of acids which are weaker than HX, suitably salts of organic acids, preferably sodium acetate, are useful acid binding agents. When using compounds of the formula (IV), wherein m is 0, it is suitable to cool the reaction mixture.

Compounds of the formula (I) obtained in their free base form can be converted, if desired, to their salts.

For the formation os salts, pharmaceutically acceptable mineral acids such as hydrochloric, hydrobromic, or sulfuric acid are most suitable for the compounds of both the formulae (I) and (III). In the cases of compounds of the formula (I), pharmaceutically acceptable organic acids, preferably methanesulfonic acid, fumaric acid and the like can be used for salt formation mainly to increase the water solubility of the compound.

The crude product can be purified by recrystallization.

According to a preferred embodiment of process b) of the invention, an aromatic ketone of the formula (II) is subjected to a condensation reaction with paraformaldehyde and a salt of a heterocyclic compound of the formula (III) under heating in a polar solvent. Ethanol or 2-propanol may suitably be used as solvents in this reaction. It is convenient to use the paraformaldehyde in an excess, commonly in an amount of 2.5 moles (calculated for the ketone) and to add it in two portions to the reaction mixture. The depolymerization of paraformaldehyde may be catalyzed by an acid, suitably by the acid used for salt formation of the heterocyclic compound of formula (III).

Instead of paraformaldehyde, formaldehyde, suitably in the form an aqueous solution, may also be employed. In this case, the reaction is carried out in the presence of a water-miscible organic solvent, preferably ethanol or methanol, in order to ensure the homogeneity of the reaction medium. Compounds being transformed in the reaction to formaldehyde and to an other compound not influencing the target reaction may also be used instead of paraformaldehyde. Formaldehyde acetals formed with lower aliphatic alcohols, preferably dimethoxy- or diethoxymethane, satisfy this demand. It is suitable to bring also the acetals in two portions into the reaction.

The progress of the reaction can be followed by using thin layer chromatography (TLC) which makes also possible to define the optimum time of reaction. In most cases, the compound of the formula (I) precipitates by cooling after termination of the reaction. Otherwise, it is suitable to promote the crystallization by adding a solvent (e.g. acetone) which is miscible with the solvent used in the reaction. When the target product of the formula (I) is hardly cuptalliazable, the base is liberated from its salt by adding an alkaline metal carbonate, e.g. potassium carbonate, in aqueous medium, then the base is extracted into an apolar solvent and after the usual operation of isolating, it is converted to the salt desired.

The recrystallization of the crude substance of formula (I) is carried out in the usual manner. It is convenient to use methanol alone or a methanol/ethanol mixture for this purpose since the crude product of formula (I) can be purified from the accompanying salt of the heterocyclic compound of formula (III) in this way. Other polar solvents such as acetone or acetonitrile may, of course, be employed. The homogeneity of the final product can be controlled by using thin layer chromatography, too.

The starting substances of the formulae (II), (III) and (IV) are generally known and can be prepared by methods usually employed for the synthesis of compounds of this type.

The compounds according to the invention can be converted into pharmaceutical compositions in a known manner. The pharmaceutical compositions may be administered in oral, rectal and/or parenteral route. For oral administration, the composition may be formulated e.g. as a tablet, dragée or capsule. In order to prepare oral compositions, e.g. lactose or starch may be used as carriers. Gelatine, carboxymethylcellulose sodium, methylcellulose, polyvinylpyrrolidone or starch gum are suitable binding or granulating agents. As disintegrating agents, mainly potato starch or microcrystalline cellulose may be added though ultraamylopectin or formaldehyde-casein and the like are also useful. Talc, colloidal silicic acid, stearin, calcium or magnesium stearate and the like are suitable anti-adhesive and sliding agents. The liquid oral compositions of the invention can be prepared in the form of e.g. a suspension, syrup or elixir which may contain water, glycols, oils, alcohols as well as colouring and flavouring additives.

Tablets may be prepared e.g. by compression following the wet granulation. The mixture of the active ingredient with the carriers and optionally with a part of the disintegrating additive is granulated with an aqueous, alcoholic or aqueous-alcoholic solution of the binding agents in a suitable apparatus, then the granulate is dried. Subsequently, after mixing the other disintegrating, sliding and anti-adhesive additives to the dried granulate, the mixture is compressed to tablets. If desired, the tablets may be provided with a groove in order to facilitate the administration. Tablets may also directly be prepared from a mixture containing the active ingredient and suitable additives. The tablets may optionally be converted to dragées by employing the commonly used pharmaceutical additives, e.g. protective, flavoring or coloring agents such as sugar, cellulose derivatives (methyl- or ethylcellulose, carboxymethylcellulose sodium and the like), polyvinylpyrrolidone, calcium phosphate, calcium carbonate, food dyes, dyeing lacquers, aromatizing agents, iron oxide pigments and the like. Capsulated compositions are prepared by filling a mixture of the active ingredient with the additives into capsules.

For rectal administration, the composition of the invention is formulated as a suppository containing a carrier mass, the so-called "adeps pro suppositorio" in addition to the active ingredient. As carriers, vegetable fats such as hardened vegetable oils, or triglycerides of $C_{12-18}$ fatty acids (preferably the carriers bearing the trade name Witepsol) may be used. The active ingredient is uniformly distributed in the molten carrier mass, then suppositories are prepared by moulding.

For parenteral administration, the composition of the invention is formulated as an injectable solution. For preparing these injectable solutions, the active ingredients are dissolved in distilled water and/or various organic solvents, e.g. glycol ethers, if desired, in the presence of solubilizing agents such as polyoxyethylene sorbitan monolaurate or monooleate or monostearate (Tween 20, Tween 60, Tween 80), respectively. The injectable solution may further contain various additives (auxiliary agents), e.g. preservatives such as ethylenediamine tetraacetate as well as pH-modifying and buffering substances or, if desired, a local anaesthetic agent such as lidocaine. Before filling into the ampouls, the injectable solution containing the composition of the invention is filtered and after filling in, it is subjected to sterilization.

On using the pharmaceutical composition of the invention, the patient is treated with a dose needed to ensure the desired effect. This dose depends upon several factors like the severity of the disease, the bodyweight of the patient and the route of administration. The dose to be used is in every case to be defined by the physician.

The invention also relates to a method for treating hypoxic brain damages of various origin such as senile dementia, Alzheimer's disease, hypoxia following atherosclerosis, multi-infarctual dementia and disturbances of the cognitive function. This method comprises administering a therapeutically effective amount of an active ingredient of the formula (I) or a pharmaceutically acceptable acid addition salt thereof to the patient.

The invention is illustrated in detail by the aid of the following non-limiting Examples. The yields given relate to compounds purified until achieving a constant melting point.

EXAMPLE 1

Preparation of 1-phenyl-3-(thiazolidinyl)propan-1-one

A suspension containing 24.0 g (0.2 mol) of acetophenone, 25.12 g (0.2 mol) of thiazolidine hydrochloride and 9.0 (0.3 mol) of paraformaldehyde in 60 ml of ethanol is heated under reflux while stirring. After one hour, an additional amount of 6.0 g (0.2 mol) of paraformaldehyde is added to the reaction mixture. After a 3-hour reaction, the mixture is cooled down, the precipitate is filtered off and washed with acetone to give 39.5 g of a crystalline product which is then recrystallized from 1400 ml of methanol to obtain 30.7 (59.6%) of uniform hydrochloride of the title compound, m.p.: 170°–171° C. The hydrobromide of the product melts at 169° C.

The compounds of formula (I), wherein $R^1$ means a carbonyl group, $R^3$, $R^4$, $R^5$, $R^6$ stand for hydrogen and m as well as n are 1, were prepared as described in Example 1 and are listed in Table III hereinafter.

(In the Tables the recrystallization solvents are given in parentheses following the melting point values.)

TABLE III

| Example No. | Ar | $R^2$ | Salt | M.p. °C. | Yield % |
|---|---|---|---|---|---|
| 2 | 4-Methylphenyl | H | HBr | 166 (EtOH-MeOH) | 48.5 |
| 2a | 4-Methylphenyl | H | HCl | 156–157 (EtOH) | |
| 3 | 3-Methylphenyl | H | HBr | 139 (EtOH) | 39.2 |
| 3a | 3-Methylphenyl | H | HCl | 138–139 (EtOH-MeOH) | |
| 4 | 2,4-Dimethylphenyl | H | HBr | 171 (acetonitrile) | 50.5 |
| 4a | 2,4-Dimethylphenyl | H | HCl | 165–166 (MeOH) | |
| 5 | 4-Phenylphenyl | H | HBr | 189 (ethanediol-EtOH) | 91.3 |
| 5a | 4-Phenylphenyl | H | HCl | 173 (ethanediol-EtOH) | |
| 6 | 2-Methoxyphenyl | H | HCl | 139–140 (MeOH-ether) | 33.4 |
| 7 | 3-Methoxyphenyl | H | HCl | 148–150 (MeOH) | 69 |
| 8 | 4-Methoxyphenyl | H | HBr | 162 (EtOH-acetone) | 69.1 |
| 9 | 3,5-Dimethoxyphenyl | H | HCl | 173 (MeOH) | 59.4 |
| 10 | 3,4-Dimethoxyphenyl | H | HCl | 171–172 (MeOH) | 78.8 |
| 11 | 2,4-Dimethoxyphenyl | H | HBr | 152–153 (MeOH-acetone) | 21.3 |
| 12 | 2-Methyl-4-methoxyphenyl | H | HCl | 153 (EtOH) | 48.6 |
| 13 | 3-Methyl-4-methoxyphenyl | H | HCl | 150–151 (EtOH) | 56 |
| 14 | 3,4,5-Trimethoxyphenyl | H | HCl | 162–163 (EtOH) | 76.2 |
| 15 | 4-(4-Fluorophenyl)-phenyl | H | HCl | 173 (decomp.) (MeOH) | 69.1 |
| 16 | 2-Flurophenyl | H | HBr | 165–167 (EtOH-acetone) | 62.5 |
| 17 | 4-Chlorophenyl | H | HBr | 189 (MeOH-EtOH) | 57.6 |
| 18 | 4-Bromophenyl | H | HBr | 189–189.5 (EtOH-acetone) | 56.9 |
| 19 | 3,4-Dichlorophenyl | H | HCl | 155–158 (MeOH) | 11 |
| 20 | 3-Nitrophenyl | H | HCl | 148–149 (MeOH) | 28 |
| 21 | 3-Chloro-4-fluorophenyl | H | HCl | 137–139 (2-propanol) | 38.2 |
| 22 | Phenyl | —CH$_3$ | HBr | 136 (2-propanol) | 64.9 |
| 23 | 4-Methylphenyl | —CH$_3$ | HBr | 145 (2-butanone-acetonitrile) | 36.4 |
| 24 | 2,4-Dimethylphenyl | —CH$_3$ | HBr | 151 (2-propanol) | 54.2 |
| 25 | 4-Methoxyphenyl | —CH$_3$ | HCl | 138–139 (acetonitrile) | 83.7 |
| 26 | 4-Benzyloxyphenyl | —CH$_3$ | HCl | 143–145 (MeOH-acetonitrile) | 66.4 |
| 27 | 4-Fluorophenyl | —CH$_3$ | HCl | 146–147 (EtOH-ether) | 32.2 |
| 28 | 4-Chlorophenyl | —CH$_3$ | HBr | 168 (acetonitrile) | 36.1 |
| 29 | 3,4-Dichlorophenyl | —CH$_3$ | HCl | 146–148 (2-propanol) | 12.4 |
| 30 | 4-Bromophenyl | —CH$_3$ | HCl | 158–160 (MeOH) | 67 |
| 31 | 4-Methylsulfinyl-phenyl | H | HCl | 165.5–166 (MeOH) | 32.5 |

TABLE III-continued

| Example No. | Ar | R² | Salt | M.p. °C. | Yield % |
|---|---|---|---|---|---|
| 32 | 4-Chlorophenyl | —C₂H₅ | HCl | 150–151 (EtOH) | 81.2 |
| 33 | 4-(4-fluorophenyl)-phenyl | —CH₃ | HCl | 164.5 (MeOH) | 50.8 |

Abbreviations used in the Table: MeOH means methanol; EtOH means ethanol

EXAMPLE 34

Preparation of
1-(4-methylthiophenyl)-3-(3-thiazolidinyl)propan-1-one

A mixture containing 16.62 g (0.1 mol) of 4-methylthioacetophenone, 12.56 g (0.1 mol) of thiazolidine hydrochloride, 4.5 g (0.15 mol) of paraformaldehyde, 35 ml of ethanol and 3 drops of concentrated hydrochloric acid is heated under reflux while stirring. After one hour, an additional amount of 3.0 g (0.1 mol) of paraformaldehyde is added to the reaction mixture. The precipitated crystals weighing 20.3 g are recrystallized from methanol and the base is liberated by adding concentrated potassium carbonate solution for further purification. The nearly colorless oily product obtained is again converted to the hydrochloride by adding ethereal hydrogen chloride solution. The hydrochloride obtained is recrystallized from methanol to obtain 12.73 g (41.9%) of hydrochloride of the title compound, m.p.: 153°–154.5° C.

EXAMPLE 35

Preparation of
1-(4-fluorophenyl)-3-(3-thiazolidinyl)propan-1-one a) A mixture containing 25.51 g (0.15 mol) of thiazolidine hydrobromide, 20.7 g (0.15 mol) of 4-fluoroacetophenone, 6.75 g (0.225 mol) of paraformaldehyde, 40 ml of ethanol and 3 drops of 48% hydrobromic acid is heated under reflux by stirring. After one hour, an additional amount of 4.50 g (0.15 mol) of paraformaldehyde is portionwise added to the reaction mixture which is then heated under reflux for an additional 2 hours. Meanwhile, a thick precipitation begins. The mixture is cooled to room temperature and filtered off to give 39.2 g of a crystalline product which is then twice recrystallized from methanol to obtain 28.6 g (59.5%) of crystalline, chromatographically homogeneous hydrobromide of the title compound, m.p.: 173.5°–174° C.

b) The hydrochloride of the title compound melts at 146.5°–147.5° C. after recrystallization from ethanol.

EXAMPLE 36

Preparation of
1-(4-piperidinophenyl)-3-(3-thiazolidinyl)propan-1-one

A mixture containing 20.4 g (0.085 mol) of 4-piperidinoacetophenone hydrochloride, 10.04 g (0.08 mol) of thiazolidine hydrochloride, 3.60 g (0.12 mol) of paraformaldehyde, 50 ml of 2-propanol and 2 drops of concentrated hydrochloric acid is heated under reflux while stirring. After one hour an additional amount of 2.40 g (0.08 mol) of paraformaldehyde is portionwise added and the reaction mixture is heated for additional 4 hours. After maintaining the mixture in a refrigerator overnight, the precipitate is filtered off to give 20.7 g of a nearly white crystalline product which is then recrystallized 3 times from methanol to obtain 8.60 g (26.2%) of the dihydrochloride of the title compound, m.p.: 156°–158° C.

EXAMPLE 37

Preparation of
1-(2-thienyl)-3-(3-thiazolidinyl)propan-1-one

A mixture containing 7.0 g (0.055 mol) of 2-acetylthiophene, 6.91 g (0.055 mol) of thiazolidine hydrochloride, 2.50 g (0.083 mol) of paraformaldehyde, 25 ml of ethanol and 2 drops of concentrated hydrochloric acid is heated under reflux while stirring. After a 3-hour reaction, an amount of 1.63 g (0.054 mol) of paraformaldehyde is portionwise added and the reaction mixture is heated for 4 additional hours. After cooling down, 50 ml of acetone are added to the mixture, the precipitate (11.28 g) is filtered off and recrystallized from methanol to give 8.0 g (55.1%) of hydrochloride of the title compound, m.p.: 176° C.

The compounds of formula (I), wherein $R^1$ stands for a carbonyl group, $R^3$, $R^4$, $R^5$ and $R^6$ are hydrogen, n as well as m are 1, which were prepared as described in Example 37, are summarized in Table IV.

TABLE IV

| Example No. | Ar | R² | Salt | M.p. °C. | Yield % |
|---|---|---|---|---|---|
| 38 | 5-Ethyl-2-thienyl | H | HCl | 151–152 (EtOH) | 41 |
| 39 | 5-Chloro-2-thienyl | H | HCl | 149–150 (MeOH) | 36.5 |
| 40 | 5-Bromo-2-thienyl | H | HCl | 162–163 (MeOH)-diisopropyl ether) | 12.3 |
| 41 | 2-Thienyl | CH₃ | HCl | 144–146 (EtOH) | 6.4 |

EXAMPLE 42

Preparation of
1-(3-methoxyphenyl)-3-(3-thiazolidinyl)propan-1-one

A mixture containing 15.02 g (0.1 mol) of 3-methoxyacetophenone, 12.56 g of thiazolidine hydrochloride, 19.02 g (0.25 mol) of dimethoxymethane, 40 ml of ethanol and 10 drops of concentrated hydrochloride acid is heated under reflux while stirring for 6 hours, then a further amount of 19.02 g (0.25 mol) of dimethoxymethane is portionwise added and the reaction mixture is heated for an additional 6 hours. On cooling down, a thick precipitate crystallizes out. After filtering the product precipitated at room temperature, 14.7 g of a substance are obtained which is then recrystallized from methanol to obtain 11.7 g (40.6%) of hydrochloride of the title compound which is completely identical with the compound described in Example 7.

EXAMPLE 43

Preparation of
1-phenyl-3-(3-thiazolidinyl)propan-1-one

The hydrochloride of the title compound is prepared from acetophenone and thiazolidine hydrochloride according to the preceding Example with a yield of 28.4%, m.p.: 169°–170° C. after recrystallization from methanol. This salt is identical to that described in Examples 1 and 61.

EXAMPLE 44

Preparation of 1-(4-fluorophenyl)-3-(tetrahydro-1,3-thiazin-3-yl)propan-1-one

A mixture containing 8.28 g (0.06 mol) of 4-fluoroacetophenone, 11.05 g (0.06 mol) of tetrahydro-1,3-thiazine hydrobromide, 2.70 g (0.09 mol) of paraformaldehyde, 25 ml ethanol and 0.1 ml of 48% hydrobromic acid is heated under reflux while stirring. After one hour an additional amount of 1.8 g (0.06 mol) of paraformaldehyde is portionwise added, the reaction mixture is heated for an additional 2 hours and then 80 ml of acetone are added. The mixture is cooled at −5° C. to give 12.73 g of product which is recrystallized from methanol to obtain 9.02 g (45.0%) of glistening crystalline hydrobromide of the title compound, m.p.: 210°–203° C.

The compounds of formula (I), wherein $R^1$ means a carbonyl group, $R^3$, $R^4$, $R^5$ and $R^6$ stand for hydrogen, m is 1 and n is 2, which were prepared as described in Example 44, are summarized in Table V.

TABLE V

| Example No. | Ar | $R^2$ | Salt | M.p. °C. | Yield % |
|---|---|---|---|---|---|
| 45 | Phenyl | H | HBr | 181 (MeOH-EtOH) | 54.7 |
| 46 | 3-Methylphenyl | H | HBr | 168 (MeOH-EtOH) | 32.7 |
| 47 | 4-Methylphenyl | H | HBr | 194 (MeOH-EtOH) | 40.0 |
| 48 | 2,4-Dimethylphenyl | H | HBr | 167–168 (MeOH-2-propanol) | 29.5 |
| 49 | 4-Phenylphenyl | H | HBr | 186–188 (MeOH-EtOH) | 59.5 |
| 50 | 3-Methoxyphenyl | H | HBr | 164–165 (EtOH) | 44.5 |
| 51 | 4-Methoxyphenyl | H | HBr | 201 (MeOH-dimethylformamide) | 65.5 |
| 52 | 3,4-Dimethoxyphenyl | H | HBr | 195 (MeOH) | 44.5 |
| 53 | 3,4,5-Trimethoxyphenyl | H | HBr | 210–212 (MeOH) | 58.6 |
| 54 | 4-Fluorophenyl | —CH$_3$ | HCl$^a$ | 166 (2-butanone-acetonitrile) | 38.8 |
| 55 | 4-Chlorophenyl | H | HBr | 205–207 (MeOH) | 58.4 |
| 56 | 4-Bromophenyl | H | HBr | 210 (MeOH) | 56.5 |
| 57 | 5-Chloro-2-thienyl | H | HBr | 197–201 (MeOH) | 47.5 |

$^a$In the preparation of this compound, the difficulty crystallizable hydrobromide is treated with potassium carbonate, the aminoketone base liberated is extracted into dichloromethane and transformed to hydrochloride in the usual manner.

EXAMPLE 58

Preparation of 1-(4-bromophenyl)-3-(3-thiazolidinyl)propan-1-one 12.56 g (0.1 mol) of thiazolidine hydrochloride, 19.9 g (0.1 mol) of 4-bromoacetophenone, 12 ml of 36% formaldehyde solution (0.144 mol), 30 ml of ethanol and 5 drops of concentrated hydrochloric acid are mixed and then heated. After a short reflux period, a homogeneous solution is formed. After a 7-hour boiling, the solution is evaporated, the oily residue is poured into 1000 ml of acetone under stirring and the precipitated starting material is filtered off. After evaporating the filtrate, the residue is recrystallized from ethanol or methanol to give the hydrochloride of the title compound, m.p.: 170° C.

EXAMPLE 59

Preparation of 2-(3-thiazolidinyl)acetophenone

A solution containing 5.67 g (0.0637 mol) of thiazolidine, 9.84 g (0.0637 mol) of ω-chloroacetophenone and 6.50 g (0.0643 mol) of triethylamine in 30 ml of acetone is left to stand at 25° C. for 12 hours. Meanwhile a thick crystalline precipitate is formed which is filtered off, washed 3 times with 50 ml of hot acetone each and the combined acetone solution is cooled down to give 5.30 g of a crystalline precipitate which is the base form of the title compound. After evaporating the mother liquor and treating the residue with ether, an additional amount of 3.00 g is obtained which is identical to the former product on the basis of thin layer chromatography. Both products are combined and converted to the hydrochloride in the usual manner. The salt obtained is recrystallized from methanol to give 4.35 g (28.0%) hydrochloride of the title compound, m.p.: 168°–171° C.

EXAMPLE 60

Preparation of 2-(3-thiazolidinyl)-4'-fluoroacetophenone

The process described in Example 59 is followed, except that ω-chloro-4-fluoroacetophenone is used as starting material to obtain the hydrochloride of the title compound in 85% yield calculated for the crude product, m.p.: 162°–163° C. after recrystallization from ethanol.

EXAMPLE 61

Preparation of 1-phenyl-3-(3-thiazolidinyl)propan-1-one

A solution containing 8.43 g (0.05 mol) of β-chloropropiophenone, 4.10 g (0.05 mol) of anhydrous sodium acetate and 4.01 g (0.045 mol) of thiazolidine in 30 ml of ethanol is stirred at 25° C. for 8 hours. After filtering off the precipitate and evaporating the solvent from the solution, the oily yellowish residue weighing 9.3 g is converted to the hydrochloride in a mixture of acetone and ether in the usual way to give 9.9 g of product. After recrystallization from methanol, the hydrochloride of the title product thus obtained melts at 170°–171° C.; it is identical to the hydrochloride described in Examples 1 and 43.

EXAMPLE 62

Preparation of
3-(5,5-dimethyl-4-ethoxycarbonyl-3-thiazolidinyl)-1-phenylpropan-1-one The hydrochloride of the title compound, m.p.: 138° C. (after recrystallization from ethanol) is obtained in 34.6% yield by using (R,S)-5,5-dimethyl-4-ethoxycarbonylthiazolidine and β-chloropropiophenone as starting substances and following the process described in Example 61.

EXAMPLE 63

Preparation of
1-(4-chlorophenyl)-3-(5,5-dimethyl-4-ethoxycarbonyl-3-thiazolidinyl)propan-1-one The hydrochloride of the title compound, m.p.: 137° C. (after recrystallization from ethanol) is obtained in 83.6% yield by using (R,S)-5,5-dimethyl-4-ethoxycarbonylthiazolidine and 4,β-dichloropropiophenone as starting substances and following the process described in Example 61.

EXAMPLE 64

Preparation of
1,2-diphenyl-3-(3-thiazolidinyl)propan-1-one

A mixture containing 9.81 g (0.05 mol) of deoxybenzoin, 5.2 g (0.04 mol) of thiazolidine hydrochloride, 2.00 g (0.067 mol) of paraformaldehyde and 0.1 ml of 37% hydrochloric acid is heated under reflux while stirring. After one hour, an additional amount of 1.00 g (0.033 mol) of paraformaldehyde is portionwise added to the homogeneous reaction mixture. After an additional 4 hours of reaction, 60 ml of acetone are added to the mixture and then cooled down in a refrigerator. The precipitated starting substance weighing 1.58 g is filtered off from the solution. After evaporating the mother liquor, the oily residue becomes solid. After treating this product with acetone, 5.9 g of a crystalline substance is obtained by filtration, which is then recrystallized first from acetonitrile and then from a 5:1 (vol./vol.) mixture of 2-propanol and ethanol to obtain 2.15 g (16.1%) of the homogeneous hydrochloride of the title compound, m.p.: 144°-146° C.

From the above pure hydrochloride, the base is liberated by adding sodium hydrogen carbonate and converted to the methanesulfonate salt, m.p.: 145°-146° C. after recrystallization from an 1:1 (vol./vol.) mixture of 2-propanol and diisopropyl ether.

EXAMPLE 65

Preparation of
1-(4-chlorophenyl)-3-(4-ethoxycarbonyl-3-thiazolidinyl)propan-1-one 10.66 g (0.025 mol) of 4,β-dichloropropiophenone are added in little portions to a suspension containing 8.06 g (0.05 mol) of 4-ethoxycarbonylthiazolidine and 4.31 g (0.0525 mol) of anhydrous sodium acetate in 30 ml of abs. ethanol at 20° to 25° C. under stirring. After stirring for 5 hours, the sodium chloride precipitate is filtered off and the filtrate is evaporated. The thick yellowish oily residue is dissolved in 90 ml of a 2:1 (vol./vol.) mixture of acetone and ether and shaken with anhydrous potassium carbonate. After filtration, the solution is acidified by ethereal hydrogen chloride solution and the oily precipitate is crystallized by adding acetone. The product obtained is recrystallized from acetone under clarifying to give 6.40 g (35.1%) of hydrochloride of the title product, m.p.: 95°-96° C.

EXAMPLE 66

Preparation of
3-(4-ethoxycarbonyl-3-thiazolidinyl)-1-phenyl-propan-1-one

The hydrochloride of the title compound is prepared as described in Example 65 in 32.7% yield, m.p.: 88.5° C. after recrystallization from the mixture of acetone and ether.

EXAMPLE 67

Preparation of
1-(4-fluorophenyl)-3-(4-ethoxycarbonyl-3-thiazolidinyl)propan-1-one The hydrochloride of the title compound is obtained in 39.1% yield, m.p.: 104°-105° C. after recrystallization from acetone.

EXAMPLE 68

Preparation of
3-(4-ethoxycarbonyl-3-thiazolidinyl)-1-(2-thienyl)propan-1-one 8.99 g (0.0515 mol) of 2-(3-chloropropionyl)thiophene are dropped to a suspension containing 7.90 g (0.049 mol) of 4-ethoxycarbonylthiazolidine and 4.22 g (0.0515 mol) of anhydrous sodium acetate in 25 ml abs. ethanol. After stirring for 9 hours, sodium chloride precipitated as fine white crystals is filtered off and, after evaporating the filtrate, etheral hydrogen chloride solution is added to the yellowish oily residue to obtain 7.65 g (46.5%) of hydrochloride of the title compound, m.p.: 97°-100° C. after recrystallization from acetone.

EXAMPLE 69

Preparation of
1-(4-chlorophenyl)-3-(5,5-dimethyl-4-methoxycarbonyl-3-thiazolidinyl)propan-1-one 10.34 g (0.0509 mol) of 4, β-dichloropropiophenone are added in little portions to the suspension of 8.50 g (0.0485 mol) of 5,5-dimethyl-4-methoxycarbonylthiazolidine and 4.18 g (0.0509 mol) of anhydrous sodium acetate in 30 ml of abs. ethanol at room temperature over 30 minutes under stirring. After stirring for an additional 8 hours, sodium chloride is filtered off and, after evaporating the filtrate, the yellow oily residue is converted to the hydrochloride by adding ethereal hydrogen chloride solution. This salt is recrystallized from ethanol to give a yield of 64.9%, m.p.: 140° C.

The compound of formula (I), wherein $R^1$ means a carbonyl group, $R^2$ and $R^6$ stand for hydrogen, $R^3$ means a methoxycarbonyl group, $R^4$ and $R^5$ are methyl groups, m and n are 1, which were prepared as described in Example 69, are summarized in Table VI.

TABLE VI

| Example No. | Ar | Salt | M.p. °C. | Yield % |
|---|---|---|---|---|
| 70 | 4-Fluorophenyl | HCl | 134–136 (EtOH) | 22.8 |
| 71 | 4-Bromophenyl | HCl | 148 (EtOH) | 62.1 |
| 72 | 2-Thienyl | HCl | 138 (EtOH-ether) | 36.1 |

EXAMPLE 73

Preparation of
1-phenyl-5-(tetrahydro-1,3-thiazin-3-yl)pent-1-en-3-one

A mixture containing 5.45 g (0.037 mol) of 4-phenyl-3-buten-2-one, 6.81 g (0.037 mol) of tetrahydro-1,3-thiazine hydrobromide, 1.50 g (0.05 mol) of paraformaldehyde, 20 ml of ethanol and 0.1 ml of 48% hydrobromic acid is heated under reflux while stirring. After one hour, an additional amount of 1.27 g (0.042 mol) of paraformaldehyde is added and the reaction mixture is refluxed for an additional 2 hours. After adding 15 ml of acetone, the reaction mixture containing a crystalline product is cooled down and filtered to give 8.1 g of crystalline hydrobromide of the title compound which is then twice recrystallized from methanol to obtain 3.95 g of pure hydrobromide. The precipitate obtained after recrystallization contains solvate methanol which can be removed at 78° C. under reduced pressure.

The yield is 31.2% calculated for the recrystallized pure product, m.p.: 179° C.

EXAMPLE 74

Preparation of
1-(4-chlorophenyl)-5-(tetrahydro-1,3-thiazin-3-yl)pent-1-en-3-one The hydrobromide of the title compound is obtained as described in Example 73 in 45.1% yield, m.p.: 181°–182° C. after recrystallization from methanol.

EXAMPLE 75

Preparation of
2-benzyl-1-phenyl-3-(3-thiazolidinyl)propan-1-one

A mixture containing 10.51 g (0.05 mol) of 1,3-diphenylpropan-1-one, 6.28 g (0.05 mol) of thiazolidine hydrochloride, 3.75 g (0.125 mol) of paraformaldehyde and 25 ml of 37% hydrochloric acid is stirred under reflux for 6 hours. After cooling down, 2.50 g of a white product precipitate from the reaction mixture which is unchanged thiazolidine hydrochloride. After evaporating the filtrate, the light yellow residue weighing 16.52 g is washed thoroughly 3 times with 20 ml of ether each. Thus, 7.80 g of a white powder-like substance are obtained which is suspended in water and the insoluble part is twice recrystallized from 2-propanol to obtain 3.50 g (20.1%) of hydrochloride of the title compound, m.p.: 134° C.

EXAMPLE 76

Preparation of
1-(4-fluorophenyl)-3-(2-methyl-3-thiazolidinyl)propan-1-one 3.73 g (0.02 mol) of β-chloro-4-fluoropropiophenone are added in little portions at room temperature to a suspension containing 2.06 g (0.02 mol) of 2-methylthiazolidine and 1.64 g (0.02 mol) of anhydrous sodium acetate in 20 ml of ethanol over 30 minutes under stirring. After stirring for an additional 3 hours, the reaction mixture is evaporated, saturated sodium hydrogen carbonate solution is added to the oily yellow residue and it is extracted twice with 30 ml of ether each. After drying and evaporating the extract, the oily yellow residue is dissolved in acetone and acidified by 48% hydrobromic acid. Thus, 4.26 g of a white crystalline product are obtained and recrystallized twice from ethanol to give 2.00 g (29.9%) of hydrobromide of the title compound, m.p.: 151°–152° C.

The compounds of formula (I), wherein $R^1$ means a carbonyl group, $R^2$, $R^3$, $R^4$ and $R^5$ are hydrogen and n as well as m are 1, which were prepared as described in Example 76, are summarized in Table VII.

TABLE VII

| Example No. | Ar | $R^6$ | Salt | M.p. °C. | Yield % |
|---|---|---|---|---|---|
| 77 | 4-Chlorophenyl | methyl | HBr | 154 (EtOH) | 56.6 |
| 78 | 4-Fluorophenyl | ethyl | HBr | 160 (EtOH) | 38.4 |
| 79 | 4-Chlorophenyl | ethyl | HBr | 152 (EtOH) | 62.4 |
| 80 | 4-Fluorophenyl | 4-fluorophenyl | HCl | 139.5 (EtOH) | 11.4 |

We claim:

1. A compound of the formula (I)

$$Ar-R^1-\underset{R^2}{\underset{|}{CH}}-(CH_2)_m-\underset{|}{\overset{R^6}{\underset{(CH)_n-\underset{R^4}{\underset{|}{C}}-R^5}{\overset{|}{N}}}}\underset{S}{\overset{CH}{\diagdown}}} \quad (I)$$

wherein
Ar stands for a phenyl, naphthyl, phenanthrenyl, or thienyl group optionally mono- or polysubstituted by halogen, $C_1$ to $C_6$alkyl, $C_1$ to $C_6$alkoxy, nitro, phenyl ($C_1$ to $C_4$ alkoxy), $C_1$ to $C_6$alkylthio, $C_1$ to $C_6$alkylsulfinyl, halophenyl, phenyl or piperidino;
$R^1$ means a carbonyl or ($C_{2-6}$alkenyl)carbonyl group;
$R^2$ stands for hydrogen, $C_{1-6}$alkyl, phenyl or phenyl ($C_{1-4}$alkyl) group;
$R^3$ means hydrogen or ($C_{1-6}$alkoxy)carbonyl group;
$R^4$ and $R^5$ stand, independently from each other, for hydrogen or a $C_{1-6}$alkyl group;
$R^6$ means hydrogen, $C_{1-6}$alkyl group or halophenyl group;
m is 0 or 1; and
n is 1 or 2,
with the proviso that $R^2$ means hydrogen when m is 0, as well as pharmaceutically acceptable acid addition salts of these compounds.

2. A compound of the formula (I) defined in claim 1, wherein
Ar stands for a phenyl or thienyl group optionally mono- or polysubstituted by halogen, $C_{1-6}$alkyl, $C_{1-6}$alkoxy, nitro, phenyl($C_{1-4}$alkoxy), $C_{1-6}$alkylthio, $C_{1-6}$alkylsulfinyl, halophenyl, phenyl or piperidino group;
$R^1$ means a carbonyl or ethylenecarbonyl group;
$R^2$ stands for hydrogen, $C_{1-4}$alkyl, phenyl or benzyl group;
$R^3$ means hydrogen or ($C_{1-4}$alkoxy)carbonyl group;
$R^4$ and $R^5$ stand, independently from each other, for hydrogen or a $C_{1-4}$alkyl group;
$R^6$ stands for hydrogen, $C_{1-4}$alkyl, group or phenyl group substituted by halogen;
m is 0 or 1; and
n is 1 or 2,
with the proviso that $R^2$ means hydrogen when m is 0 as well as pharmaceutically acceptable acid addition salts of these compounds.

3. 1-(4-chlorophenyl)-3-(3-thiazolidinyl)propan-1-one or a pharmaceutically acceptable acid addition salt thereof as defined in claim 1.

4. 1-(4-fluorophenyl)-3-(3-thiazolidinyl)propan-1-one or a pharmaceutically acceptable acid addition salt thereof as defined in claim 1.

5. 1-(2-thienyl)-3-(3-thiazolidinyl)propan-1-one or a pharmaceutically acceptable acid addition salt thereof as defined in claim 1.

6. 1-(4-fluorophenyl)-3-(5,5-dimethyl-4-methoxycarbonyl-3-thiazolidinyl)propan-1-one or a pharmaceutically acceptable acid addition salt thereof as defined in claim 1.

7. 1-(4-bromophenyl)-3-(3-thiazolidinyl)propan-1-one or a pharmaceutically acceptable acid addition salt thereof as defined in claim 1.

8. 1-(4-bromophenyl)-2-methyl-3-(3-thiazolidinyl)propan-1-one or a pharmaceutically acceptable acid addition salt thereof as defined in claim 1.

9. 1-phenyl-3-(3-thiazolidinyl)propan-1-one or a pharmaceutically acceptable acid addition salt thereof as defined in claim 1.

10. 1-phenyl-2-methyl-3-(3-thiazolidinyl)propan-1-one or a pharmaceutically acceptable acid addition salt thereof as defined in claim 1.

11. 1-(4-phenylphenyl)-3-(tetrahydro-1,3-thiazin-3-yl)propan-1-one or a pharmaceutically acceptable acid addition salt thereof as defined in claim 1.

12. 1-(5-ethyl-2-thienyl)-3-(3-thiazolidinyl)propan-1-one or a pharmaceutically acceptable acid addition salt thereof as defined in claim 1.

13. A compound defined in claim 1 selected from the group consisting of
1-(4-methylthiophenyl)-3-(3-thiazolidinyl)propan-1-one,
1-(4-chlorophenyl)-3-(3-thiazolidinyl)propan-1-one,
1-(4-fluorophenyl)-3-(3-thiazolidinyl)propan-1-one,
1-(2-thienyl)-3-(3-thiazolidinyl)propan-1-one,
1-(4-fluorophenyl)-3-(5,5-dimethyl-4-methoxycarbonyl-3-thiazolidinyl)propan-1-one,
1-(4-bromophenyl)-3-(3-thiazolidinyl)propan-1-one,
1-(2-methyl-4-methoxyphenyl)-3-(3-thiazolidinyl)-propan-1-one,
1-(4-bromophenyl)-2-methyl-3-(3-thiazolidinyl)propan-1-one,
1-(5-chloro-2-thienyl)-3-(3-thiazolidinyl)propan-1-one,
1-phenyl-3-(3-thiazolidinyl)propan-1-one,
1-phenyl-2-methyl-3-(3-thiazolidinyl)propan-1-one,
1-(4-phenylphenyl)-3-(tetrahydro-1,3-thiazin-3-yl)propan-1-one and
1-(5-ethyl-2-thienyl)-3-(3-thiazolidinyl)propan-1-one or a pharmaceutically acceptable acid addition salt thereof.

14. A pharmaceutical composition, which comprises an active ingredient a compound of the formula (I), defined in claim 1 or a pharmaceutically acceptable acid addition salt thereof in admixture with a pharmaceutically acceptable inert carrier.

15. A composition as claimed in claim 14, which comprises as active ingredient a compound of the formula (I), as defined in claim 2, or a pharmaceutically acceptable acid addition salt thereof in admixture with carriers or additives commonly used in the pharmaceutical industry.

16. Method for treating patients suffering from hypoxic brain damage which comprises the step of administering to said patient a therapeutically effective amount of the compound of the formula (I), as defined in claim 1, or a pharmaceutically acceptable acid addition salt thereof.

* * * * *